United States Patent [19]

Schumann

[11] Patent Number: Plant 7,385

[45] Date of Patent: Nov. 27, 1990

[54] GERANIUM PLANT NAMED FISWIG

[75] Inventor: Ingeborg Schumann, Hoehr-Grenzhausen, Fed. Rep. of Germany

[73] Assignee: Florfis AG, Binningen, Switzerland

[21] Appl. No.: 426,173

[22] Filed: Oct. 25, 1989

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner, Schwartz, Jeffery, Schwaab, Mack, Blumenthal & Evans

[57] ABSTRACT

A new and distinct cultivar of Geranium plant named Fiswig, particularly characterized by the combined features of large, single carmine red flowers, floriferous habit, dark green foliage, good rain resistance as well as good heat tolerance, good transport ability, and fast rooting.

1 Drawing Sheet

The present invention comprises a new and distinct cultivar of Geranium, botanically known as *Pelargonium zonale,* and hereinafter referred to by the cultivar name Fiswig.

Fiswig is a product of a planned breeding program which had the objective of creating new geranium cultivars with a new bright color in combination with dark green foliage, fast rooting, very good weather resistance and better chlorophyll quality for better transportation.

Fiswig was originated from a hybridization made by the inventor in a controlled breeding program in Hillscheid, Federal Republic of Germany in 1982. The female parent was an inbred line (second generation) from a cultivar designated No. 94, characterized by its rose colored single flowers, rich flowering, and very compact habit. The male parent of Fiswig was the cultivar pelfi ® Bern, having dark green foliage, red colored single flowers, tall habit, and inferior branching.

Fiswig was discovered and selected as one flowering plant within the progeny of the stated cross by Ingeborg Schumann in May 1983 in a controlled environment in Hillscheid, Federal Republic of Germany.

The first act of asexual reproduction of Fiswig was accomplished when vegetative cuttings were taken from the initial selection in February 1984 in a controlled environment in Hillscheid, Federal Republic of Germany by, or under the supervision of, Ingeborg Schumann.

Horticultural examination of selected units initiated in Spring 1984 and continuing thereafter has demonstrated that the combination of characteristics as herein disclosed for Fiswig are firmly fixed and are retained through successive generations of asexual reproduction.

Fiswig has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse conditions which approximate those generally used in commercial practice.

The following traits have been repeatedly observed and are determined to be basic characteristics of Fiswig, which, in combination, distinguish this Geranium as a new and distinct cultivar:

1. Dark green foliage in combination with a new carmine red color.
2. Large single, round flowers.
3. Better chlorophyll quality for better transportation.
4. Fast rooting.
5. Early flowering.
6. No shattering with good rain resistance.
7. Maintains quality during shipping.
8. Good tolerance to heat.

The unique combination of characteristics of Fiswig make this new cultivar difficult to compare with known zonal cultivars.

The accompanying color photographic drawing shows typical flower and foliage characteristics of Fiswig, with the colors being as true as possible with illustrations of this type.

In the following description color references are made to The Royal Horticultural Society Colour Chart (R.H.S.) and in certain instances to the Horticultural Color Chart (H.C.C.). The color values were determined between 9:00 a.m. and 9:30 a.m. indoors on May 29, 1987 under 40,000 Lux light intensity at Hillscheid, Federal Republic of Germany.

Classification:

*Botanical.*—*Pelargonium zonale* l'hert. cv Fiswig.
*Commercial.*—Zonal Geranium.

INFLORESCENCE

A. Umbel:
- *Average diameter.*—Indoor, 12.0 cm; outdoor, 12.6 cm.
- *Average depth.*—Indoor, 5.4 cm; outdoor, 6.0 cm.
- *Peduncle length.*—Indoor, 14.5 cm; outdoor, 15.0 cm.
- *Pedicel length.*—Indoor, 4.0 cm; outdoor, 3.9 cm.

B. Corolla:
- *Average diameter.*—Indoor, 4.5 cm; outdoor, 4.5 cm.
- *Form.*—Round, single.
- *Color (general tonality from a distance of three meters).*—Carmine red, HCC 22.
- *Color (upper surface).*—RHS 52A; HCC 22.
- *Color (under surface).*—RHS 52A; HCC 22.
- *Sepals.*—Green.

C. Bud:

*Shape.*—Elliptic.

*Color.*—Green.

*Pedicels.*—Light red, some with "spur" (swelling).

D. Reproductive organs:

*Androecium.*—8–10 anthers.

*Gynoecium.*—5 lobed stigma.

E. Spring flowering response period: In Hillscheid, Federal Republic of Germany in 1988, 63% of plants with at least 1 flower opened 12 weeks after planting of unrooted cuttings.

F. Outdoor flower production: The flower count in 1988 in Hillscheid, Federal Republic of Germany indicated between 45 and 55 flowers per plant for June through October observation period.

G. Durability: Good rain resistance; no shattering.

PLANT

A. Foliage:

*Form.*—Kidney shaped.

*Margin.*—Bicrenate.

*Color (upper surface).*—Medium-dark green.

*Color (zonation).*—Weak dark green zonation.

*Tolerance to botrytis.*—Very good.

B. General appearance and form:

*Internode length.*—Short.

*Branching pattern.*—3.2 branches per plant after 13 weeks of growing time from unrooted cuttings.

*Height.*—28 cm on average.

I claim:

1. A new and distinct cultivar of Geranium plant named Fiswig, as illustrated and described.

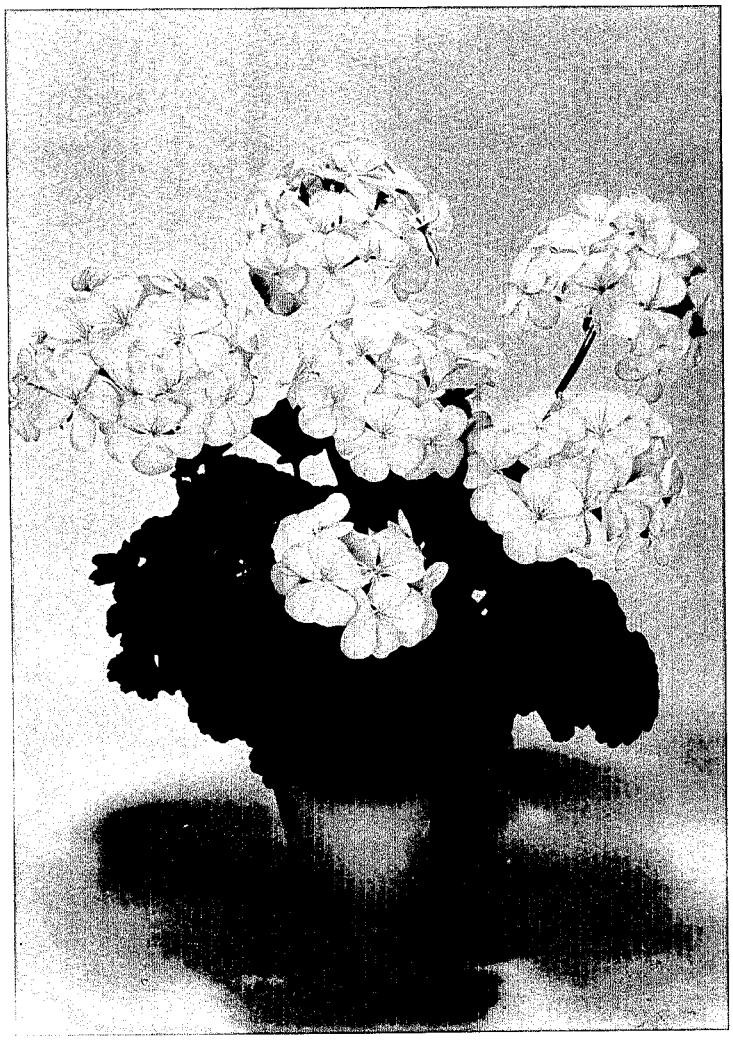

* * * * *